United States Patent
Rock et al.

(10) Patent No.: US 11,166,945 B2
(45) Date of Patent: Nov. 9, 2021

(54) ANIMAL TREATMENTS

(71) Applicant: NewMarket Pharmaceuticals LLC, Trenton, NJ (US)

(72) Inventors: David Rock, California, MO (US); Mark Ridall, Skillman, NJ (US)

(73) Assignee: NewMarket Pharmaceuticals LLC, Trenton, NJ (US)

( * ) Notice: Subject to any disclaimer, the term of this patent is extended or adjusted under 35 U.S.C. 154(b) by 0 days.

(21) Appl. No.: 16/886,093

(22) Filed: May 28, 2020

(65) Prior Publication Data

US 2020/0289487 A1     Sep. 17, 2020

Related U.S. Application Data

(63) Continuation of application No. 16/014,290, filed on Jun. 21, 2018, now Pat. No. 10,702,509, which is a continuation of application No. 14/275,019, filed on May 12, 2014, now Pat. No. 10,022,361, which is a continuation of application No. 13/343,692, filed on Jan. 4, 2012, now Pat. No. 8,722,636.

(60) Provisional application No. 61/437,763, filed on Jan. 31, 2011.

(51) Int. Cl.

| | |
|---|---|
| A61K 31/4439 | (2006.01) |
| A61K 31/135 | (2006.01) |
| A61K 9/00 | (2006.01) |
| C07D 307/52 | (2006.01) |
| C07D 401/12 | (2006.01) |
| A61K 31/155 | (2006.01) |
| A61K 31/341 | (2006.01) |
| A61K 31/403 | (2006.01) |
| A61K 31/4164 | (2006.01) |
| A61K 31/44 | (2006.01) |
| A61K 31/5415 | (2006.01) |
| A61K 31/7048 | (2006.01) |
| A61K 31/137 | (2006.01) |
| A61K 31/4174 | (2006.01) |
| A61K 31/635 | (2006.01) |

(52) U.S. Cl.
CPC ........ *A61K 31/4439* (2013.01); *A61K 9/0053* (2013.01); *A61K 31/135* (2013.01); *A61K 31/137* (2013.01); *A61K 31/155* (2013.01); *A61K 31/341* (2013.01); *A61K 31/403* (2013.01); *A61K 31/4164* (2013.01); *A61K 31/4174* (2013.01); *A61K 31/44* (2013.01); *A61K 31/5415* (2013.01); *A61K 31/635* (2013.01); *A61K 31/7048* (2013.01); *C07D 307/52* (2013.01); *C07D 401/12* (2013.01)

(58) Field of Classification Search
CPC .............. A61K 31/4439; A61K 31/635; A61K 31/341; A61K 31/403; A61K 31/4164; A61K 31/44; A61K 31/5415; A61K 31/7048; A61K 31/135; A61K 9/0053; A61K 31/137; A61K 31/4174; A61K 31/155; C07D 401/12; C07D 307/52
USPC .......................................................... 514/30
See application file for complete search history.

(56) References Cited

U.S. PATENT DOCUMENTS

| | | |
|---|---|---|
| 6,193,999 B1 | 2/2001 | Gennadios |
| 6,471,992 B1 | 10/2002 | Yoo et al. |
| 6,596,311 B1 | 7/2003 | Dobetti |
| 6,709,669 B1 | 3/2004 | Murray |
| 7,122,198 B1 | 10/2006 | Singh et al. |
| 7,939,561 B2 | 5/2011 | Schellenger et al. |
| 8,545,879 B2 | 10/2013 | Burns et al. |
| 8,647,668 B2 | 2/2014 | Tanaka et al. |
| 8,722,636 B2 | 5/2014 | Rock |
| 9,402,835 B2 | 8/2016 | Rock |
| 10,022,361 B2 | 7/2018 | Rock |
| 10,064,849 B2 | 9/2018 | Ridall et al. |
| 10,695,332 B2 | 6/2020 | Ridall et al. |
| 10,702,509 B2 | 7/2020 | Rock et al. |
| 2002/0035076 A1 | 3/2002 | Parks |
| 2003/0031711 A1 | 2/2003 | Fara et al. |
| 2004/0248942 A1 | 12/2004 | Hepburn et al. |
| 2007/0042023 A1 | 2/2007 | Puri et al. |
| 2007/0184106 A1 | 8/2007 | Schellenger et al. |
| 2007/0275058 A1 | 11/2007 | Tanaka et al. |
| 2008/0096971 A1* | 4/2008 | Baxter .................... A61P 29/02 514/646 |

(Continued)

FOREIGN PATENT DOCUMENTS

| | | |
|---|---|---|
| CA | 2369951 | 11/2000 |
| EP | 1 891 937 | 2/2008 |

(Continued)

OTHER PUBLICATIONS

Arvanitoyannis et al., "Edible films made from hydroxypropyl starch and gelatin and plasticized by polyols and water," Carbohydrate Polymers 36:105-119 (1998).

(Continued)

*Primary Examiner* — Yih-Horng Shiao

(74) *Attorney, Agent, or Firm* — Bond, Schoeneck & King, PLLC

(57) ABSTRACT

Compositions and methods for the treatment and control of various conditions in an animal which comprises administering to said animal an effective amount of a immediate release composition of about 0.5% to 50% wt/wt of active ingredient together with excipients to a total of about 100%, wherein said composition dissolves in a relatively short period of time, e.g., 75 seconds or less, 5 seconds or less, or 3 seconds or less, upon administration to said animal.

21 Claims, No Drawings

(56) References Cited

U.S. PATENT DOCUMENTS

| | | | |
|---|---|---|---|
| 2011/0256229 A1 | 10/2011 | Nystrom et al. | |
| 2012/0219628 A1* | 8/2012 | Lim | A61K 31/519 424/484 |
| 2015/0133504 A1 | 5/2015 | Ridall et al. | |
| 2018/0360816 A1 | 12/2018 | Rock et al. | |
| 2018/0369221 A1 | 12/2018 | Ridall et al. | |

FOREIGN PATENT DOCUMENTS

| | | |
|---|---|---|
| WO | WO 00/50038 | 8/2000 |
| WO | WO 02/058735 | 8/2002 |
| WO | WO 2004/067004 | 8/2004 |
| WO | WO 2006/048501 | 5/2006 |
| WO | WO 2007/002125 | 1/2007 |
| WO | WO 2012/106058 | 8/2012 |
| WO | WO 2013/165468 | 11/2013 |

OTHER PUBLICATIONS

Chubineh et al.: "Proton Pump Inhibitors: the Good the Bad and the Unwanted," Southern Medical Journal, vol. 105, No. 11, pp. 613-618, Nov. 2012.

Extended European Search Report in EP 12875765 (corresponds to PCT/US2012/070031) dated Aug. 31, 2015, 9 pages.

Glossary of Medical Education Terms, Institute of International Medical Education, http://www.iime.org/glossary.htm, accessed on Jan. 2013, 43 pages.

International Preliminary Report on Patentability for International Application No. PCT/US2012/020242 dated Aug. 6, 2013, 6 pages.

International Search Report for International Application No. PCT/US2012/020242 dated Aug. 30, 2012, 5 pages.

International Search Report in PCT Application No. PCT/US2012/070031 dated Feb. 26, 2013, 3 pages.

International Preliminary Report on Patentability in PCT Application No. PCT/US2012/070031 dated Nov. 4, 2014, 6 pages.

Liles et al. The use of non-steroidal anti-inflammatory drugs for the relief of pain in laboratory rodents and rabbits. Laboratory Animals 26:241-255, 1992.

Mona Nagar et al.: "Formulation, Evaluation and Comparison of Fast-Dissolving Tablet of Nimesulide by Using Crospovidone as Superdisintegrant," International Journal of Pharmaceutical Sciences and Drug Research, 2009, 1(3), pp. 172-175.

R. Panigrahi et al.: "A Review on Fast Dissolving Tablets," WebMedCentral Pharmaceutical Sciences, Sep. 29, 2010, 1(9), pp. 1-15.

www.avma.org/isues/drugs/compouncing/veterinary_compounding_brochure.asp, Veterinary Compounding Brochure, American Veterinary Medical Association (AVMA) Jun. 2001, 6 pages.

www.fda.gov/AnimalVeterinary/NewsEvents/FDAVeterinarianNewsletter/ucm10026-8.htm, Mar./Apr. 2003, 4 pages.

\* cited by examiner

ANIMAL TREATMENTS

RELATED APPLICATIONS

This application is a continuation of U.S. application Ser. No. 16/014,290 filed on Jun. 21, 2018, which is a continuation of U.S. application Ser. No. 14/275,019 filed on May 12, 2014; which is now U.S. Pat. No. 10,022,361 issued on Jul. 17, 2018, which is a continuation of U.S. application Ser. No. 13/343,692 filed on Jan. 4, 2012, which is now U.S. Pat. No. 8,722,636, issued on May 13, 2014, which claims the benefit of U.S. Provisional Application No. 61/437,763 filed on Jan. 31, 2011. The entire contents of these prior applications are incorporated herein by reference.

BACKGROUND

Therapeutic agents for animals, for example equines, bovines, canines, felines, ovines, and porcines, suffer from numerous drawbacks for a variety of reasons. For example, injectable formulations, which may be preferred because they provide rapid onset of activity, are most preferably administered in an environment of cleanliness to prevent infections at the injection site. However, with domesticated animals this may be difficult to ensure in a typical barn, farm, field or racetrack environment where such injectable formulations may be administered. A further drawback of an injectable formulation is that a typical injectable therapeutic may suffer from a relatively short duration of activity. Oral dosing formulations for animals suffer from different drawbacks, in that the animal can spit the formulation out of its mouth before it is ingested, resulting in a loss of the full dosage. In a circumstance where the oral formulation is administered by intubation, the dosing may suffer from variability of bioavailability due to the inherent and unique characteristics of each animal's digestive system, i.e., the amount of food in the animal's stomach, the length of time since its last feeding, and the animal's levels of digestive enzymes, which may vary due to other environmental conditions, etc. Further limitations of existing formulations include stability of the active ingredient in the formulation, and possible inadvertent or incorrect dosing of the human administrator with the drug substance.

Most veterinary therapeutics are off-shoots of drugs developed for humans rather than being specifically developed for the unique characteristics of a specific animal, for example equines, bovines, canines, felines, ovines, and porcines. Due to the high costs associated with developing formulations tailored precisely for animals, and obtaining regulatory approval of such formulations for animals, many veterinarians have a limited repertoire of drugs to utilize in the therapy of various animal diseases. Thus, the FDA allows "extra-label use" of human drugs. See, "Extra-label Drug Use in Veterinary Medicine", available from www.fda.gov/AnimalVeterinary/NewsEvents/FDAVeterinarianNewsletter/ucm1 00268.htm. This practice has resulted in formulations of human drugs by compounding pharmacists at the request of veterinarians, i.e, so-called "custom compounding," in order to enlarge therapeutic armamentarium available to veterinarians. See, for instance, the brochure published by the FDA entitled "Veterinary Compounding" available from www.avma.org/issues/druas/compoundina/veterinary_compounding brochure.asp Therefore, there exists a need to provide improved therapeutic methods for animals, for example equines, bovines, ovines, canines, felines and porcines which obviate many of the disadvantages and side effects of the commonly used injectable and oral formulations.

There further exists a need to provide methods for the treatment of animals, for example equines, bovines, canines, felines, ovines, and porcines with drug products which give an earlier onset of action, along with a concomitant reduction in side effects including risk of infection at injection sites or bioavailability issues resultant from the absorption of the drug from the digestive tract of the animal.

There also exists a need to provide methods which enable treatment of the animal patient which reliably and predictably provides for regulatory clearance of the drug. For example, in animals participating in competition, the drug clears the animal's system so that it may undergo treatment without drug residues remaining which would disqualify it from competition. Since the clearance of a drug administered via the methods of the present disclosure is more rapid, the animal may only need to discontinue therapy for a relatively short period of time, thus minimizing the effect of discontinuance for several days, resulting in a re-establishment or increased severity of the disease under treatment.

Disclosed herein are animal treatment methods and compositions, for example for the treatment of animals, for example equines, bovines, canines, felines, ovines, and porcines. Various embodiments comprise administration of a therapeutic agent into the bloodstream of the animal via a formulation administered via the oral cavity. In various embodiments, a majority of the formulation may be absorbed prior to reaching the gastric mucosa. In certain embodiments, the formulation may be adapted for animals, for example equines, bovines, canines, felines, ovines, and porcines to dissolve in a relatively short period of time, e.g., 75 seconds or less. Such administration of the formulation may, in at least certain embodiments, result in faster onset of the therapy, diminished occurrences of the side-effects due to non-uniformity of bioavailability of the active agent, and/or more accurate dosing, which may, in at least some embodiments, result in dose lowering. Further, in at lease some embodiments, such administration may result in a greater portion of the therapeutic agent actually being directly introduced systemically into the circulatory system for its therapeutic effect.

Also disclosed herein are methods for the treatment and control of various diseases afflicting animals, for example equines, bovines, canines, felines, ovines, and porcines, with improved safety for the both the animal and the person administering the therapeutic agent.

In at least certain exemplary embodiments, the compositions and methods are useful for administration to humans.

DETAILED DESCRIPTION

Therapeutic agents, such as, for example, clenbuterol, imiprazole, omeprazole, detomidine, acepromazine, flunixin, moxidectin and praziquantel have been typically administered orally. For example, in domesticated animals these agents may be administered in the form of feed concentrates, feed additives, tablets, oblets, boluses, gels, pastes, or the like, or have been administered parenterally as an injectable. Of the above-mentioned formulation types, arguably the most suitable for ease of administration, efficiency, and effective dosage, as well as economic and practical application of the endoparasiticidal agents moxidectin and praziquantel which are often included, is an oral gel or paste. Feed additives and feed concentrates are unsuitable due to the lack of stability of many active ingredients in the presence of moisture and/or excipients utilized in feeds, and the lack of packaging and storage conditions ensuring accurate dosing to animals of variable weight. Tablets, boluses, oblets, and drenches are often cumbersome to administer to large numbers of animals effectively, and parenteral injection is more stressful for the animal and the handler.

Further, oral administration of therapeutic agents suffer the disadvantages of exposure to the gastric environment which results in degradation metabolism when absorbed through the gastric mucosa and gastric and/or hepatic metabolism, resulting in reduced levels of the therapeutic agent available for the treatment of the disease.

Surprisingly, it has now been found that therapeutic agents may be formulated in a so-called "fast-acting" or "immediate release" formulation and conveniently administered to the circulatory system of the animal via a formulation administered via the oral cavity, the majority of which is absorbed prior to the gastric mucosa. In various embodiments the thereapeutic agents may be adapted for animals, such as, for example equines, bovines, canines, felines, ovines, and/or porcines to afford therapeutic effects without the concomitant disadvantages of the prior art formulations. In further embodiments, the formulations may be adapted for humans.

Non-limiting exemplary fast release formulations may include those such as the multiparticulate fast disintegrating tablets disclosed, for instance in U.S. Pat. No. 6,596,311; the so-called rapidly dispersing "3-D platform", disclosed in U.S. Pat. No. 6,471,992; pectin-based dissolvable films, such as disclosed in US2007/0042023; the teachings of all of which are incorporated herein by reference. In the veterinary therapeutic technology space, such fast release formulations were originally developed for human use and were designed to be administered orally, rather than directly to the circulatory system of the recipient via a formulation administered via the oral cavity, the majority of which is absorbed prior to the gastric mucosa, thus providing direct systemic introduction ("DSI").

These fast release formulations may comprise the active therapeutic agent, typically in combination with acceptable excipients such as gelatin, mannitol or another sugar alcohol, together with suitable sweetening agents, such as aspartame, and suitable flavoring agents such as mint flavoring, for example peppermint, fruit flavors, and/or meat/fish flavors.

The fast/immediate release formulations described herein are manufactured using suitable excipients in accordance with the techniques and processing disclosed in the aforementioned U.S. Pat. No. 6,596,311. In at least certain embodiments, the formulations are rapid release formulations, having faster release times that typical formulations for non-controlled release (e.g., immediate release). In various embodiments, the active ingredient, either as a free base or a water-soluble salt, may be dissolved or suspended in water or another suitable solvent, together with various excipients, and subjected to a process such as freeze-drying in order to provide immediate release compositions in which the active ingredient is relatively stable, and which can provide, upon administration, therapeutically useful levels of the active ingredient.

In a typical formulation according to various embodiments of the disclosure, the active ingredient may comprise from about 0.5 to about 50% by weight of the composition, such as, for example, about 1.0 to about 10% by weight of the composition, or about 5% by weight of the composition, depending upon the particular active chosen and the total amount of the active ingredient which is needed to administer to the animal under treatment.

In human dosing, traditional immediate release formulations provide for the nonmodified, as opposed to controlled or sustained, release of the active ingredient in the stomach. Traditional sublingual doses dissolve quickly under the tongue, but none-the-less can be thought of as immediate-release formulations. In recent years, "rapid release" technologies have been developed which speed up the release profile over traditional formulations, particularly in the stomach. The compositions and methods of administration contemplated herein involve both immediate release dosing and rapid release dosing to the circulatory system of the animal in a formulation administered via the oral cavity, the majority of which is absorbed prior to the gastric: mucosa, adapted for humans, equines, bovines, canines, felines, ovines, and porcines. Unless specifically noted otherwise, "immediate release" shall include traditional immediate release (i.e., not controlled or sustained release).

We have now found that administering therapeutic agents via the oral cavity, where the majority is absorbed prior to the gastric mucosa, i.e., under the tongue (sublingual), on the top of the tongue, and/or between the cheek (buccal), to animals, results in rapid onset of activity, more accurate and lowered dosing, an absence or diminishment of side-effects, and greater safety to both the animal and the administrator of the formulation.

As used herein, the term "oral cavity" means that portion of the alimentary canal from the orifice conventionally referred to as the mouth, including, for example the area distally from the mouth to the esophagus and all tissues including, for example the mucal membranes, epithelium, cheek, tongue (e.g., under, on or around the tongue) and gums.

As used herein, the term "non-gastric mucosa" refers to the pre-gastric mucosal cells, e.g., oral mucosa, including the mucous membrane beneath the tongue, and/or the buccal mucosa at the inside of the cheek and gum and absorption sites in the esopaghus.

As used herein, the term "pre-gastric" refers to all parts of the alimentary canal beginning at the mouth and continuing to the juncture with the secretory stomach.

As used herein, "Direct Systemic Introduction" ("DSI"), means administering one or more therapeutically active agent(s) directly to the circulatory system of an animal via a formulation administered and absorbed in the oral cavity and/or the non-gastric mucosa. DSI may, in at least some embodiments, provide relatively high systemic concentrations of the active agents, e.g. by allowing agents to pass directly into the systemic circulation avoiding the destructive activities in the digestive tract by gastric breakdown, metabolism in the wall of the GI tract and first pass metabolism by the liver. DSI may result in higher systemic availability of therapeutic agents in the animal for their desired therapeutic effects, when compared to products formulated in conventional oral delivery systems.

DSI can provide advantages over traditional oral, intravenous, intramuscular, and subcutaneous routes of administration, in that more of the drug may be available systemically for its desired therapeutic effects. For example, in equines, DSI can provide more rapid metabolic clearance of the drug, resulting in a shortened withdrawal time to clear the animal for performance racing. See, e.g., "Equine Drug Testing and Therapeutic Medication Regulation: 2009 Policy of the National Horsemen's Benevolent and Protective Association, Inc." edited by Thomas Tobin & Kent H. Stirling, which discusses the necessary withdrawal times for performance animals.

The DSI formulations disclosed herein may dissolve rapidly when in contact with the oral cavity and/or the non-gastric mucosa. In some embodiments, the immediate release formulations contemplated herein will dissolve when in contact with the oral cavity and/or the non-gastric mucosa in about 90 seconds or less. In some embodiments, the DSI formulation will dissolve in about 75 seconds or less, such as in about 60 seconds or less about 45 seconds or less, about 30 seconds or less, or about 5 seconds or less. In some embodiments, the DSI formulation dissolves in less than about 3 seconds.

A further benefit of the DSI dosing of an animal is that the person administering may be able to more quickly titrate an appropriate dosage for the level and severity of the condition of the animal. Using typical routes of administration, due to metabolic disposition and the overall health of the animal, it may take a practitioner a period of several days to achieve an appropriate dose to treat and control a condition. One advantage of a DSI formulation is that the practitioner may reliably assume therapeutic effects within a short period of time, and adjust the level of administration of the drug, as needed.

In at least some embodiments, DSI formulations permit a shorter withdrawal time from treatment than with some conventional oral dosing regimens. By way of example only, typically, an equine patient will need to be withdrawn from many medications for periods ranging from 24-72 hours prior to performance racing. This results in interruption of the therapy, and can lead to a worsening of the existing disease, or at the least, a slower recovery than if the withdrawal had not occurred. In many cases using DSI therapy, however, the equine patient may only need to discontinue the therapy for a period as short as 0-12 hours or not at all, depending upon the particular therapeutic agent being utilized in the methods of the present disclosure.

In at least one exemplary embodiment, the methods herein are administered to the circulatory system of the animal via a DSI formulation administered and absorbed in the oral cavity and/or the non-gastric mucosa, adapted for humans, equines, bovines, canines, felines, ovines, and porcines, resulting in rapid absorption of the active ingredient and faster clearance. Due to both administration and absorption to the oral cavity and/or the non-gastric mucosa, the resultant effect is DSI.

Therapeutic agents which can be utilized in DSI formulations and administered via the described methods include, but are not limited to, antibiotic, antibacterial, antifungal, antiviral, anti-inflammatory, anesthetic, analgesic, anti-allergic, corticosteroid, and mixtures thereof at any proportion. The concentration of said agents may be adapted to exert a therapeutic effect on a disease when applied to an afflicted animal, or human, by a practitioner skilled in the art.

A non-limiting list of exemplary therapeutic agents include abacavir, acebutolol, acepromazine, acrivastine, alatrofloxacin, albuterol, albendazole, alprazolam, alprenolol, amantadine, amiloride, aminoglutethimide, amiodarone, amitriptyline, amlodipine, amodiaquine, amoxapine, amphetamine, amphotericin, amprenavir, amrinone, amsacrine, astemizole, atenolol, atropine, azathioprine, azelastine, azithromycin, baclofen, benethamine, benidipine, benzhexol, benznidazole, benztropine, biperiden, bisacodyl, bisanthrene, brolliazepam, bromocriptine, bromperidol, brompheniramine, brotizolam, bupropion, butenafine, butoconazole, cambendazole, camptothecin, carbinoxamine, cephadrine, cephalexin, cetrizine, cinnarizine, chlorambucil, chlorpheniramine, chlorproguanil, chlordiazepoxide, chlorpromazine, chlorprothixene, chloroquine, cimetidine, ciprofloxacin, cisapride, citalopram, clarithromycin, clemastine, clemizole, clenbuterol, clofazimine, clomiphene, clonazepam, clopidogrel, clozapine, clotiazepam, clotrimazole, codeine, cyclizine, cyproheptadine, dacarbazine, darodipine, decoquinate, delavirdine, demeclocycline, detomidine, dexamphetamine, dexchlorpheniramine, dexfenfluramine, diamorphine, diazepam, diethylpropion, dihydrocodeine, dihydroergotamine, diltiazem, dimenhydrinate, diphenhydramine, diphenoxylate, diphenylimidazole, diphenylpyraline, dipyridamole, dirithromycin, disopyramide, dolasetron, domperidone, donepezil, doxazosin, doxycycline, droperidol, econazole, efavirenz, ellipticine, enalapril, enoxacin, enrofloxacin, eperisone, ephedrine, ergotamine, erythromycin, ethambutol, ethionamide, ethopropazine, etoperidone, famotidine, felodipine, fenbendazole, fenfluramine, fenoldopam, fentanyl, fexofenadine, flecainide, flucytosine, flunarizine, flunitrazepam, flunixin, fluopromazine, fluoxetine, fluphenthixol, fluphenthixol decanoate, fluphenazine, fluphenazine decanoate, flurazepam, flurithromycin, frovatriptan, gabapentin, granisetron, grepafloxacin, guanabenz, halofantrine, haloperidol, hyoscyamine, imipenem, imiprazole, indinavir, irinotecan, isoxazole, isoxsuprine HCl, isradipine, itraconazole, ketoconazole, ketotifen, labetalol, lamivudine, lanosprazole, leflunomide, levofloxacin, lisinopril, lomefloxacin, loperamide, loratadine, lorazepam, lormetazepam, lysuride, mepacrine, maprotiline, mazindol, mebendazole, meclizine, medazepam, mefloquine, melonicam, meptazinol, mercaptopurine, mesalamine, mesoridazine, metformin, methadone, methaqualone, methylphenidate, methylphenobarbital, methysergide, metoclopramide, metoprolol, metronidazole, mianserin, miconazole, midazolam, miglitol, minoxidil, misoprostol, mitomycins, mitoxantrone, molindone, montelukast, morphine, moxifloxacin, nadolol, nalbuphine, naratriptan, natamycin, nefazodone, nelfinavir, nevirapine, nicardipine, nicotine, nifedipine, nimodipine, nimorazole, nisoldipine, nitrazepam, nitrofurazone, nizatidine, norfloxacin, nortriptyline, nystatin, ofloxacin, olanzapine, omeprazole, ondansetron, omidazole, oxamniquine, oxantel, oxatomide, oxazepam, oxfendazole, oxiconazole, oxprenolol, oxybutynin, oxyphencyclimine, paroxetine, pentazocine, pentoxifylline, perchlorperazine, perfloxacin, pergolide, perphenazine, phenbenzamine, pheniramine, phenoxybenzamine, phentermine, physostigmine, pimozide, pindolol, pizotifen, pramipexol, pranlukast, praziquantel, prazosin, procarbazine, prochlorperazine, proguanil, propranolol, pseudoephedrine, pyrantel, pyrimethamine, quetiapine, quinidine, quinine, raloxifene, ranitidine, remifentanil, repaglinide, reserpine, ricobendazole, rifabutin, rifampin, rifapentine, rimantadine, risperidone, ritonavir, rizatriptan, ropinirole, rosiglitazone, roxaditine, roxithromycin, salbutamol, saquinavir, selegiline, sertraline, sibutramine, sildenafil, sparfloxacin, spiramycins, stavudine, sulconazole, sulphasalazine, sulpiride, sumatriptan, tacrine, tamoxifen, tamsulosin, temazepam, terazosin, terbinafine, terbutaline, terconazole, terfenadine, tetramisole, thiabendazole, thioguanine, thioridazine, tiagabine, ticlopidine, timolol, tinidazole, tioconazole, tirofiban, tizanidine, tolterodine, topotecan, toremifene, tramadol, trazodone, triamterene, triazolam, trifluoperazine, trimethoprim, trimipramine, tromethamine, tropicamide, trovafloxacin, vancomycin, venlafaxine, vigabatrin, vinblastine, vincristine, vinorelbine, vitamin KS, vitamin K6, vitamin K7, zafirlukast, zolmitriptan, zolpidem, zopiclone, acetazolamide, acetohexamide, acepromazine, acrivastine, alatrofloxacin, albuterol, alclofenac, aloxiprin, alprostadil, amodiaquine, amphotericin, amylobarbital, aspirin, atorvastatin, atovaquone, baclofen, barbital, benazepril, bezafibrate, bromfenac, bumetanide, butobarbital, candesartan, capsaicin, captopril, cefazolin, celecoxib, cephadrine, cephalexin, cerivastatin, cetrizine, chlorambucil, chlorothiazide, chlorpropamide, chlorthalidone, cinoxacin, ciprofloxacin, clinofibrate, cloxacillin, cromoglicate, cromolyn, dantrolene, dichlorophen, diclofenac, dicloxacillin, dicumarol, diflunisal, dimenhydrinate, divalproex, docusate, dronabinol, enoximone, enalapril, enoxacin, enrofloxacin, epalrestat, eposartan, essential fatty acids, estramustine, ethacrynic acid, ethotoin, etodolac, etoposide, fenbufen, fenoprofen, fexofenadine, fluconazole, flurbiprofen, fluvastatin, fosinopril, fosphenytoin, fumagillin, furosemide, gabapentin, gemfibrozil, gliclazide, glipizide, glybenclamide, glyburide, glimepiride, grepafloxacin, ibufenac, ibuprofen, imipenem, indomethacin, irbesartan, isotretinoin, ketoprofen, ketorolac, lamotrigine, levofloxacin, levothyroxine, lisinopril, lomefloxacin, losartan, lovastatin, meclofenamic acid, mefenamic acid, mesalamine, methotrexate, metolazone, montelukast, nalidixic acid, naproxen, natamycin, nimesulide, nitrofurantoin, non-essential fatty acids, norfloxacin, nystatin, ofloxacin, oxacillin, oxaprozin, oxyphenbutazone, penicillins, pentobarbital, perfloxacin, phenobarbital, phenytoin, pioglitazone, piroxicam, pramipexol, pranlukast, pravastatin, probenecid, probucol, propofol, propylthiouracil, quinapril, rabeprazole, repaglinide, rifampin, rifapentine, sparfloxacin, sulfabenzamide, sulfacetamide, sulfadiazine, sulfadoxine, sulfamerazine, sulfamethoxazole, sulfafurazole, sulfapyridine, sulfasalazine, sulindac, sulphasalazine, sulthiame, telmisartan, teniposide, terbutaline, tetrahydrocannabinol, tirofiban, tolazamide, tolbutamide, tolcapone, tolmetin, tretinoin, troglitazone, trovafloxacin, undecenoic acid, ursodeoxycholic acid, valproic acid, valsartan, vancomycin, verteporfin, vigabatrin, vitamin K-S(II), zafirlukast, and pharmaceutically acceptable oil-soluble derivatives and salts thereof. For example, such salts include but are not limited to clenbuterol HCl, flunixin meglumine, acepromazine maleate, detomidine HCl.

Further are included altrenogest, amprolium, bacitracin zinc plus nicarbazin, butorphanol tartrate, cefevecin sodium, ceftiofur, cephapirin sodium, chlortetracycline, deracoxib, deslorelin acetate, dexmedetomidine hydrochloride, firocoxib, florfenicol, gentamicin sulfate and betamethasone valerate, gonadotropin releasing factor-diphtheria toxoid conjugate, griseofulvin, hyaluronate sodium, imidacloprid, Ian phosphate, lasalocid, masitinib mesylate, melengestroJ acetate and zilpaterol hydrochloride, milbemycin oxime, monensin usp, orbifloxacin, oxytetracycline, pirlimycin hydrochloride, polysulfated glycosaminoglycan, progesterone, protamine zinc, ractopamine hydrochloride, ractopamine hydrochloride, robenacoxib, romycin, selamectin, semduramicin sodium biomass plus virginiamycin, sevoflurane, sevoflurane, spinosad, sulfachlorpyridazine sodium, tiamulin, toceranib, trilostane, tulathromycin, tylosin phosphate, tylosin tartrate, and any pharmaceutically acceptable substantially oil-soluble derivatives and salts thereof.

Suitable anti-infective agents include, but are not limited to antibacterial, antifungal, antiviral, and anti-parasitic agents.

Specific macrolide antibiotics useful in various embodiments include but are not limited to erythromycin; sulfonamide (in its base form), such as sulfanilamide, sulfadiazine and sulfacetamide; mupirocin; tetracyclines, such as tetracycline and doxycycline; synthetic and semi-synthesic penicillins and beta-lactams; cloramphenicol; imidazoles; dicarboxylic acids, such as azelaic acid; salicylates; peptide antibiotics; and cyclic peptides, such as cyclosporine, tacrolimus, pimecrolimus and sirolimus (rapamycin). These antibiotics may be used in the treatment of various antibacterial, antifungal, antiviral and parasitic infections in humans, equines, bovines, ovines, canines, felines and porcines. Another embodiment according to the present disclosure utilizes an anti-inflammatory or anti-allergic as a therapeutic agent. Anti-inflammatory agents include but are not limited to corticosteroids, non-steroidal anti-inflammatory drugs (NSAIDs), antihistamines, immunosuppressant agents, immunomodulators; and any combination thereof at a therapeutically effective concentration.

Another class of anti-inflammatory agents, which may be useful in various embodiments of the present disclosure, includes the nonsteroidal anti-inflammatory agents (NSAIDs). The variety of compounds encompassed by this group is well-known to those skilled in the art. Some non-steroidal anti-inflammatory agents useful in the compositions described herein include, but are not limited to: oxicams, such as piroxicam, isoxicam, tenoxicam, sudoxicam; salicylates, such as salicylic acid, ethyl salicylate, methyl salicylate, aspirin, disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; and pyrazoles, such as phenylbutazone, oxyphenbutazone, feprazone, azapropazone, and trimethazone.

Other therapeutic agents include diphenhydramine, doxepin, phrilamine maleate, chlorpheniramine and tripelennamine, phenothiazines, promethazine hydrochloride and dimethindene maleate. These active agents, as well as additional antihistamines can also be incorporated into a DSI formulation and utilized in the methods described herein to treat various respiratory and allergic conditions in animals.

In at least one embodiment, the therapeutic compositions described herein comprise an anti-inflammatory or antiallergic agent, wherein said agent reduces the occurrence of pro-inflammatory cytokines or inhibits the effect of pro-inflammatory cytokines. In one embodiment, the compositions and methods described herein include mixtures of anti-inflammatory agents, as well as the dermatologically acceptable salts, esters, amides, prodrugs and derivatives of these agents. Such agents may be utilized to treat numerous conditions where inflammation is present, either as a result of disease or injury, and include, but are not limited to muscle strains, arthritic conditions, joint dysplasia, infections etc.

Administration of a DSI formulation (e.g., immediate or rapid release formulation) according to various embodiments, e.g. comprising a safe and effective dose of an NSAID, can be useful in the prevention and/or alleviation of the symptoms of rheumatoid arthritis, osteoarthritis and pain. NSAIDs, incorporated in a fast acting formulation and administered according to the methods of the present disclosure can be also used in the treatment of dermatological disorders, such as acne, rosacea, hair growth disorders, actinic keratosis and certain skin cancer conditions.

In one embodiment, the therapeutic methods disclosed herein comprise administering a DSI formulation (e.g., immediate or rapid release formulation) comprising an anti-inflammatory or antiallergic agent, wherein said agent reduces the occurrence of pro-inflammatory cytokines or inhibits the effect of pro-inflammatory cytokines. Mixtures of such anti-inflammatory agents may also be employed, as well as the dermatologically acceptable salts, esters, am ides, prodrugs and derivatives of these agents.

In one embodiment, the therapeutic methods disclosed herein comprise administering a DSI formulation (e.g., immediate or rapid release formulation) comprising a safe and effective dose of an NSAID, for the prevention and/or alleviation of the symptoms of rheumatoid arthritis, osteoarthritis and/or pain.

In one embodiment, the therapeutic methods disclosed herein comprise administering a DSI formulation (e.g., immediate or rapid release formulation) for the use in treating coat disorders comprising administering immunosuppressant agents, immunoregulating agents and immunomodulators are chemically or biologically-derived agents that modify the immune response or the functioning of the immune system (as by the stimulation of antibody formation or the inhibition of white blood cell activity).

Immunosuppressant agents and immunomodulators include, among other options, cyclic peptides, such as cyclosporine, tacrolimus, tresperimus, pimecrolimus, sirolimus (rapamycin), verolimus, laflunimus, laquinimod and imiquimod. Such compounds, delivered sublingually in a immediate release formulation, are especially advantageous in coat disorders, where the large coat areas are to be treated.

In one embodiment, the therapeutic methods disclosed herein comprise administering a DSI formulation (e.g., immediate or rapid release formulation) comprising a safe and effective amount of a topical anesthetic. Examples of suitable anesthetic drugs include benzocaine, lidocaine, bupivacaine, chlorprocaine, dibucaine, etidocaine, mepivacaine, tetracaine, dyclonine, hexylcaine, procaine, cocaine, ketamine, pramoxine, phenol, and pharmaceutically acceptable salts thereof. In one embodiment of the therapeutic methods, mixtures of such anesthetic agents are administered and are synergistically beneficial.

In one embodiment, the therapeutic methods disclosed herein comprise administering a DSI formulation (e.g., immediate or rapid release formulation) comprising anti-cancer agents to treat animal malignant tumors.

Advantageously, in at least some embodiments, DSI compositions according to the disclosure may ensure complete and accurate dosing with less stress for both the animal and the animal handler. Further, the methods of the disclosure may allow for higher concentrations of active ingredients, thereby minimizing the need for multiple dosing.

In one embodiment, DSI provides for methods of treating and controlling conditions in an animal, comprising administering to said animal an effective amount of a therapeutic agent in a DSI composition (e.g., immediate or rapid release formulation) which comprises: about 0.5% to about 50% wt/wt of active ingredient together with excipients to a total of about 100% wt/wt.

In further embodiments, DSI provides for methods of treating and controlling conditions in an animal, comprising administering to said animal an effective amount of a therapeutic agent in a DSI composition (e.g., immediate or rapid release formulation) which comprises, for example, about 1.0% to about 10% wt/wt of active ingredient together with excipients to a total of about 100% wt/wt.

In further embodiments, DSI provides for methods of treating and controlling conditions in an animal, comprising administering to said animal an effective amount of a therapeutic agent in a DSI composition (e.g., immediate or rapid release formulation) which comprises, for example, about 5% by weight of active ingredient together with excipients to a total of about 100% wt/wt.

Effective amounts may vary according to various factors, such as, but not limited to, the general health of the animal, the degree or severity of the particular disease under treatment, the age of the animal, the organs infected or infested, and the like. In at least one embodiment of the therapeutic methods disclosed herein, the amount of the DSI compositions is sufficient to provide therapeutic levels of the active ingredient as quickly as possible.

In an exemplary embodiment where the active ingredient is clenbuterol, the amount of a non-limiting and exemplary DSI composition administered is that sufficient to provide about 0.2 meg/kg to about 3.0 meg/kg of active ingredient per body weight of the animal and about 0.4 meg/kg to about 1.5 meg/kg, most preferably about 0.8 meg/kg of active ingredient per body weight of the animal. In one embodiment the composition comprises about 0.36 mg clenbuterol/tablet. For example, in one embodiment, the composition comprises 0.363 mg of clenbuterol per tablet to treat recurrent airway inflammation (RAI) in horses by significantly increasing mucociliary transport in horses with RAI.

In further embodiments, the methods of treatment disclosed herein comprise administering DSI compositions of clenbuterol for the treatment of a central nervous system disorder. For example, in one embodiment, the methods of treatment comprise administering DSI compositions of clenbuterol for treating Parkinson's Disease to a patient in need thereof.

In a further exemplary embodiment where the active ingredient is omeprazole, the amount of said DSI composition administered is that sufficient to provide about 0.5 mg/kg to about 8.0 mg/kg of active ingredient per body weight of the animal and about 1.0 mg/kg to about 6.0 mg/kg, about 4.0 mg/kg of active ingredient per body weight of the animal, with an approximate amount of about 350-550 mg omeprazole/dose. Imiprazole, or histamine type-2 receptor antagonists (such as cimetidine or ranitidine), or other proton pump inhibitors such as pantoprazole are used to suppress gastric acidity and to heal and prevent gastric ulcers.

In a further exemplary embodiment, where the active ingredient is omeprazole, the amount of said DSI composition administered is that sufficient to provide omeprazole at a pH of greater than about 6. In other exemplary embodiments, omeprazole is administered at a pH of about 10.

When the active ingredient is tramadol, the amount of the DSI composition administered is sufficient to provide about 0.5 mg/kg to about 8.0 mg/kg of active ingredient per body weight of the animal and about 0.75 mg/kg to about 6.0 mg/kg, about 1 to about 4 mg/kg of active ingredient per body weight of the animal. In one embodiment the amount of tramadol DSI composition is about 4.5 to about 18 mg tramadol/tablet. In at least one embodiment, the therapeutic methods comprise administering tramadol for the treatment of pain. In at least one further embodiment, the therapeutic methods comprise administering codeine for the treatment of pain. In yet a further embodiment, the therapeutic methods comprise administering codeine for the treatment of coughing as an analgesic. In yet a further embodiment, the therapeutic methods comprise administering codeine for the treatment of coughing. In yet a further embodiment, the therapeutic methods comprise administering codeine for the induction of sedation before surgery and/or as a supplement to anesthesia.

When the active ingredient is guanabenz, for example, the amount of the DSI composition administered may be chosen such that it is sufficient to provide about 0.33 mg/kg to, about 2.0 mg/kg of active ingredient per body weight of the animal and about 0.44 mg/kg to about 1.0 mg/kg, about 0.66 mg/kg of active ingredient per body weight of the animal, with an approximate amount of about 300 mg guanabenz/tablet. In one exemplary embodiment, the therapeutic methods comprise administering guanabenz to an animal to reduce the blood pressure in the animal's pulmonary circulatory tract and thereby reduce the incidence and/or severity of exercise-induced pulmonary hemorrhage. In a further exemplary embodiment, the therapeutic methods comprise administering guanabenz to an animal as a sedative.

When the active ingredient is furosemide, for example, the amount of the DSI composition administered may be chosen such that it is sufficient to provide about 0.10 mg/kg to about 2.0 mg/kg of active ingredient per body weight of the animal and about 0.25 mg/kg to about 1.5 mg/kg. In one exemplary embodiment, the therapeutic methods comprise administering furosemide to an animal about 0.5 to about 1.0 mg/kg of active ingredient per body weight of the animal, with an approximate amount of about 50 to about 450 mg furosemide/tablet. In a further exemplary embodiment, the therapeutic methods comprise administering furosemide to an animal as a diuretic. In one embodiment the therapeutic methods comprise administering furosemide to an animal to treat pulmonary edema. In yet a further embodiment, the therapeutic methods comprise administering furosemide to an animal to treat congestive heart failure in combination with other drugs. In yet a further embodiment, the therapeutic methods comprise administering furosemide to an animal to treat allergic reactions. In yet further embodiments, the therapeutic methods comprise administering furosemide to an animal to reduce the incidence of exercise-induced pulmonary hemorrhage (EIPH) (a.k.a. "bleeding") by animals during races.

When the active ingredient is ivermectin, for example, the amount of the DSI composition administered may be chosen such that it is sufficient to provide about 0.05 mg/kg to about 0.4 mg/kg of active ingredient per body weight of the animal and about 0.1 mg/kg to about 0.3 mg/kg, about 0.2 mg/kg of active ingredient per body weight of the animal, with an approximate amount of about 90 mg ivermectin/tablet. In one exemplary embodiment, the therapeutic methods comprise administering ivermectin to an animal to treat numerous parasites in animals including humans, horses, cows, dogs, pigs and sheep such as large strongyles, small strongyles, pinworms, ascarids, hairworms, large-mouth stomach worms, bats, lungworms, intestinal threadworms, to name a few. In an exemplary embodiment, the therapeutic methods comprise administering ivermectin to an animal to control summer sores caused by bots. In yet a further exemplary embodiment, the therapeutic methods comprise administering ivermectin to an animal to treat dermatitis caused by neck threadworms.

When the active ingredient is carprofen, for example, the amount of OSI composition administered may be chosen such that it is sufficient to provide about 0.2 mg/kg to about 4.0 mg/kg of active ingredient per body weight of the animal and about 0.45 mg/kg to about 2.0 mg/kg, about 1.0 mg/kg of active ingredient per body weight of the animal, with an approximate amount of about 400 mg carprofen/tablet. In one embodiment, for example, the therapeutic method comprises administering carprofen to an animal to treat arthritis in animals. As used herein "arthritis" includes both short term, for joint pain or post-operative inflammation, or for day-to-day relief from the pain and inflammation associated with osteoarthritis, hip dysplasia, and other forms of joint deterioration. Its use may reduce inflammation by inhibiting the production of COX-2 and other sources of inflammatory prostaglandins.

When the active ingredient is flunixin meglumine, for example, the amount of the OSI composition administered may be chosen such that it is sufficient to provide about 0.25 mg/kg to about 4.4 mg/kg of active ingredient per body weight of the animal and about 0.55 mg/kg to about 2.2 mg/kg, about 1.1 mg/kg of active ingredient per body weight of the animal, with an approximate amount of about 500 mg flunixin meglemune/tablet. In one exemplary embodiment, the therapeutic method comprises administering flunixin meglumine to an animal to treat pain. In yet another embodiment, the therapeutic method comprises administering flunixin meglumine to an animal for treating colic. In a further exemplary embodiment, the therapeutic method comprises administering flunixin meglumine to an animal for treating septic/endotoxic shock due to any gastrointestinal (GI) insult either post-surgical or medical such as in cases of peritonitis or diarrhea. In yet a further exemplary embodiment, the therapeutic method comprises administering flunixin meglumine to an animal for treating used as an anti-inflammatory to treat painful conditions of the eye including corneal ulcers, uveitis, conjunctivitis and before and after eye surgery. In yet a further exemplary embodiment, the therapeutic method comprises administering flunixin meglumine to an animal for treating fevers due to viral or bacterial infections.

Other active ingredients for use in the methods disclosed herein include, but are not limited to, those such as albuterol, cromolyn, dantrolene, domperidone, isoxsuprine HCl, ketoprofen, misoprostol, pergolide, phenylbutazone, phenytoin and reserpine.

As described herein, homeothermic animals suitable for treatment in the disclosed methods include, for example, humans, equine, bovine, ovine, swine, caprine, canine, feline or the like animals, or any for whom metabolic disposition of an active is problematic, or for which initial dose titration may pose risks, or which is otherwise undesirable.

The above disclosed doses and dosage ranges are not intended to be limiting. A practitioner skilled in the art may likewise administer suitable DSI compositions (e.g., immediate or rapid release formulation) in single or divided doses, according to the desired therapeutic effect. Thus, in certain clinical situations it may be desirable to administer compositions to give initial high levels of the active ingredient, followed by lower dose maintenance doses.

In the compositions and methods described herein, where a particular compound is recited applicants contemplate isolated enantiomers and mixtures thereof in any proportions. For example, where the term "clenbuterol" is used, applicants contemplate either or both of the R. and/or S-enantiomers.

It is to be understood that the foregoing description is exemplary and explanatory only, and not to be interpreted as restrictive of the disclosure. Various modifications of this disclosure, in addition to those shown and described herein, will become apparent to those skilled in the art from the following examples and the foregoing description. Such modifications are also intended to fall within the scope of the present disclosure. Other embodiments will be apparent to those skilled in the art from consideration of the disclosure and practice of the various exemplary embodiments disclosed herein.

It is also to be understood that, as used herein the terms "the," "a," or "an," mean "at least one," and should not be limited to "only one" unless explicitly indicated to the contrary. Thus, for example, the use of "a therapeutic agent" is intended to mean at least one therapeutic agent.

Unless otherwise indicated, all numbers used in the specification and claims are to be understood as being modified in all instances by the term "about," whether or not so stated. It should also be understood that the precise numerical values used in the specification and claims form additional embodiments of the disclosure, and are intended to include any ranges which can be narrowed to any two end points disclosed within the exemplary ranges and values provided. Efforts have been made to ensure the accuracy of the numerical values disclosed herein. Any measured numerical value, however, can inherently contain certain errors resulting from the standard deviation found in its respective measuring technique.

What is claimed is:

1. A method of treating recurrent airway inflammation in an animal in need thereof, the method comprising:
    determining a dose of clenbuterol required; and
    administering orally to a pre-gastric mucosal cell of the animal a Direct Systemic Introduction (DSI) composition comprising clenbuterol,
    wherein the DSI composition in the animal's oral cavity is dissolved in less than about 75 seconds, and
    wherein the required dose of clenbuterol is determined by greater than 50% of the administered clenbuterol being detected in the animal's circulatory system via the pre-gastric mucosal cells lining the animal's alimentary canal prior to the animal's secretory stomach.

2. The method according to claim 1, wherein the DSI composition is dissolved in less than about 30 seconds.

3. The method according to claim 1, wherein the DSI composition is dissolved in less than about 5 seconds.

4. The method according to claim 1, wherein the clenbuterol is present in the DSI composition in an amount ranging from about 0.5% to about 50% by weight of the overall composition.

5. The method according to claim 1, wherein the clenbuterol is in the form of a free base; a water soluble salt; or an isolated single enantiomer or mixture thereof.

6. The method according to claim 1, wherein the animal is human.

7. The method according to claim 1, wherein the animal is an equine.

8. The method according to claim 1, wherein the DSI composition further comprises at least one excipient.

9. The method according to claim 1, wherein the DSI composition provides an immediate release of clenbuterol.

10. The method according to claim 1, wherein the DSI composition is in the form of a tablet comprising about 0.36 mg of clenbuterol.

11. The method according to claim 1, wherein the DSI composition is formulated to provide about 0.2 mcg/kg to about 3.0 mcg/kg of clenbuterol per body weight of the animal.

12. A method of treating a central nervous system disorder in an animal in need thereof, the method comprising:
    determining a dose of clenbuterol required; and
    administering orally to a pre-gastric mucosal cell of the animal a Direct Systemic Introduction (DSI) composition comprising clenbuterol,
    wherein the DSI composition in the animal's oral cavity is dissolved in less than about 75 seconds, and
    wherein the required dose of clenbuterol is determined by greater than 50% of the administered clenbuterol being detected in the animal's circulatory system via the pre-gastric mucosal cells lining the animal's alimentary canal prior to the animal's secretory stomach.

13. The method according to claim 12, wherein the central nervous system disorder is Parkinson's Disease.

14. The method according to claim 12, wherein the DSI composition is dissolved in less than about 30 seconds.

15. The method according to claim 12, wherein the DSI composition is dissolved in less than about 5 seconds.

16. The method according to claim 12, wherein the clenbuterol is present in the DSI composition in an amount ranging from about 0.5% to about 50% by weight of the overall composition.

17. The method according to claim 12, wherein the clenbuterol is in the form of a free base; a water soluble salt; or an isolated single enantiomer or mixture thereof.

18. The method according to claim 12, wherein the animal is human.

19. The method according to claim 12, wherein the animal is an equine.

20. The method according to claim 12, wherein the DSI composition further comprises at least one excipient.

21. The method according to claim 12, wherein the DSI composition provides an immediate release of clenbuterol.

* * * * *